United States Patent [19]

Bainbridge

[11] 4,345,154

[45] Aug. 17, 1982

[54] BIAS-COMPENSATED, IONIZATION SENSOR FOR GASEOUS MEDIA AND METHOD FOR ATTAINING PROPER BIAS FOR SAME

[75] Inventor: Augustus S. Bainbridge, Baltimore, Md.

[73] Assignee: The United States of America as represented by the Secretary of the Army, Washington, D.C.

[21] Appl. No.: 264,873

[22] Filed: May 18, 1981

Related U.S. Application Data

[63] Continuation-in-part of Ser. No. 3,436, Jan. 12, 1979, abandoned.

[51] Int. Cl.³ .............................................. H01J 39/28
[52] U.S. Cl. .................................... 250/375; 250/379; 324/464
[58] Field of Search ............... 250/380, 379, 386, 381, 250/375, 382, 383, 384, 252; 324/459, 464, 469

[56] References Cited

U.S. PATENT DOCUMENTS

| | | | |
|---|---|---|---|
| 2,485,516 | 10/1949 | Thompson | 250/379 |
| 2,740,894 | 4/1956 | Deisler et al. | 250/381 |
| 2,837,656 | 6/1958 | Hendee et al. | 250/379 |
| 3,028,490 | 4/1962 | Guilleux | 250/381 |
| 3,084,255 | 4/1963 | Brinkerhoff et al. | 250/380 |
| 3,417,238 | 12/1968 | Hartmann | 250/379 |

*Primary Examiner*—Alfred E. Smith
*Assistant Examiner*—Carolyn E. Fields
*Attorney, Agent, or Firm*—Nathan Edelberg; Robert P. Gibson; Max Yarmovsky

[57] ABSTRACT

An ionization detector unit innovatively adapted to provide mobility to the unit and to render it especially suitable for convenient "field-use" in point-source sampling and monitoring of the compositional characteristics of a gaseous medium such as, for example, the ambient atmosphere, and in emitting a discernible electrical signal which in response to a perceptible change in the compositional characteristics in the medium being monitored by the detector will be altered sufficiently to activate, or trigger, a suitable alarm or warning mechanism.

The detector unit includes an ionization sensor cell for emitting an output signal and is powered by a suitable electrical source such as, for example, a miniature power source, and means for delivering or feeding to the sensor cell a representative stream or flow of the gaseous medium to be ionization monitored, and features a method and means for effectively compensating for variations and/or fluctuations in the electrical output signal emitted by the sensor cell as a consequent result of variations and/or fluctuations occurring in the rate of flow of the medium being delivered to and monitored thereby. The featured means is in the form of a low-voltage, battery-operated, bias device having a selectively predetermined, optimum, electrical resistance and a diode controlled voltage output operationally interconnected between one terminal or electrode of the sensor cell and an electrical ground.

An innovative process and apparatus also are disclosed for determining the most effective bias voltage and preselected resistance to be provided by the biasing means.

19 Claims, 4 Drawing Figures

BIAS-COMPENSATED, IONIZATION SENSOR FOR GASEOUS MEDIA AND METHOD FOR ATTAINING PROPER BIAS FOR SAME

GOVERNMENTAL INTEREST

The invention described herein may be manufactured, used and licensed by or for the Government for governmental purposes without payment to me of any royalty thereon.

CROSS-REFERENCE TO RELATED APPLICATION

This application is a continuation-in-part of copending application, Ser. No. 3,436, filed Jan. 12, 1979, now abandoned.

BACKGROUND OF THE INVENTION

1. Field of the Invention

The invention pertains generally to detection devices utilizing ionization sensor cells for monitoring gaseous media and for detecting changes in the compositional characteristics thereof. In more particular respects, the present invention relates to a process and apparatus for rendering such devices more suitable for reliable field-use, and particularly more suitable for personal field-use for the detection of changes in the normal compositional characteristics of the ambient atmosphere such as may result, for example, from the presence in the ambient atmosphere of dangerous or harmful substances.

2. Description of the Prior Art

Heretofore, ionization sensor cells commonly have been used in detector units for detecting the presence of harmful gases and vapors. Moreover, such detector units have commonly utilized one or more such cells for testing sample gas and vapors fed thereto by aspirator pumps. Additionally, such detector units have conventionally included supplemental electronic elements such as amplifiers, recorders, etc., to set off or activate one or more warning alarms in response to the detection of harmful gases and/or vapors sensed to be present in excess of a preselected concentration level.

In the past, before my invention, it was found that when variations in the rate of flow of the gas or vapor being detected occurred, erratic changes or fluctuations in the electrical output signals emitted by the sensor cell took place which, of course, interfere with and obstruct the reliability of any output signal characteristics which are attributable to the composition of the medium being monitored. Consequently, the detector unit was not adequately reliable for its intended purpose and false alarms were not uncommon.

Various corrective measures were taken. The sensor cell outputs were placed in opposition to each other so that a cancellation effect would occur. Although this technique, adopted by the U.S. Air Force, has met with marginal success, it has required the use of an excessive number of cells, amplifiers and accessory components, as well as undesirably high power supplies which ordinarily are not available from small, lightweight power sources. Consequently, the detector units were inordinately heavy, bulky and unsuitable for use as a lightweight, portable device for personal field-use. Moreover, high voltages on the terminals were commonplace.

SUMMARY OF THE INVENTION

Unlike the aforementioned detector units of the past, I have found that economy, sensor sensitivity, and operational reliability can be achieved in a relatively simple, compact and light-weight, low-voltage, detector unit if, in accordance with the innovative apparatus and process steps of the present invention, a small, bias voltage is impressed upon the ionization sensor cell by virtue of the unexpectedly simple, effective and innovative expedient of interconnecting a source of low-voltage bias between an electric ground and one sensor terminal of the ionization sensor cell. To this end, according to one aspect of the invention, while the sensor cell is monitoring a selected gaseous medium supplied thereto at varying rates of flow, a source of low-voltage, bias voltage of selectively adjustable voltage potential and selectively reversible polarity is impressed upon the ionization sensor cell. By selective adjustment of the voltage potential and polarity of the bias voltage, the appropriate polarity and optimum voltage potential may be obtained for effectively stabilizing, or eliminating, fluctuations and/or variations in the electrical output signal emitted from the sensor cell. Otherwise stated, the small, bias voltage is adjusted so that minimum variation occurs in the output signal emitted from the sensor cell over a range of varied flow rates of the gaseous medium being tested or monitored.

Therefore, because I have found that stability can be had by adjustment of the cell to a quiescent zone which occurs with the application of a certain amount of bias voltage for a given cell, my innovative breakthrough has come about.

In keeping with my discovery, a sensor cell apparatus for use in a detector for harmful gases and vapors, according to the present invention, comprises an ionization cell in operative combination with low-voltage bias means operatively interconnected with the ionization cell for stabilizing the output signal emitted therefrom and optionally transmitted to appropriate preamplification and indicating and/or warning devices or gear.

The ionization cell is of conventional type with terminal voltage application. It is basically intended to create current flow in response to ionization of a gaseous medium flowing therethrough, and being of conventional-type fluctuations or variations in the rate of flow of the gaseous medium cause corresponding fluctuations or variations in the extent or level of ionization occurring within and being sensed by the cell. Consequently, the resultant output voltages, which, of course, are directly indicative of and responsive to the occurrence of variations in the ionization level of the gaseous medium within the sensor cell, also correspondingly fluctuate. To compensate for such fluctuations in the output voltage emitted from the sensor cell, one of the terminals of the sensor cell is, in accordance with the present invention, subjected to a selective series of bias voltages at each of a selective series of sensor cell flow rates selected to be representative of the variant flow rates occurring during operational use of the sensor cell. This is done to selectively obtain the best, or optimum, bias-voltage setting with which to eliminate, or suppress, appreciable variation in the output signal emitted from the sensor cell in response to sizable fluctuations in flow rate of the gaseous medium. One such a bias voltage is determined for the cell under varying flow conditions, optimum operational results are readily attainable. Determination of the appropriate, or optimum, bias voltage is readily obtained by interconnecting a bias voltage test device between one output terminal of the sensor cell and an electrical ground. The test device preferably comprises a low-voltage power source such as a 2 volt battery, a variable resistor for varying the battery voltage impressed upon the sensor cell terminal and optionally a double-pole, double-throw switch for reversal of current flow from the test device to the sensor cell.

Having once established the optimum bias voltage for stabilization of the output voltage emitted from the sensor cell, the test device, in accordance with another aspect of the invention, may optionally be replaced with a miniature biasing device for providing the test-determined, optimum bias voltage. For this purpose, an innovative biasing device has been devised comprising a low-voltage source, such as, for example, a small or miniature battery having a nongrounded one of a pair of output terminals adapted to be interconnected with one of the sensor cell output terminals and having the other output terminal adapted to be electrically grounded; a current limiting electrical resistor having a preselected resistance interconnected with the nongrounded output terminal of the low-voltage battery; a zener diode interconnected with the load side of the electrical resistor and the grounded output terminal of the low-voltage battery; and, optionally a capacitor interconnected in parallel with the zener diode.

DETAILED DESCRIPTION OF THE INVENTION

Figure 1:
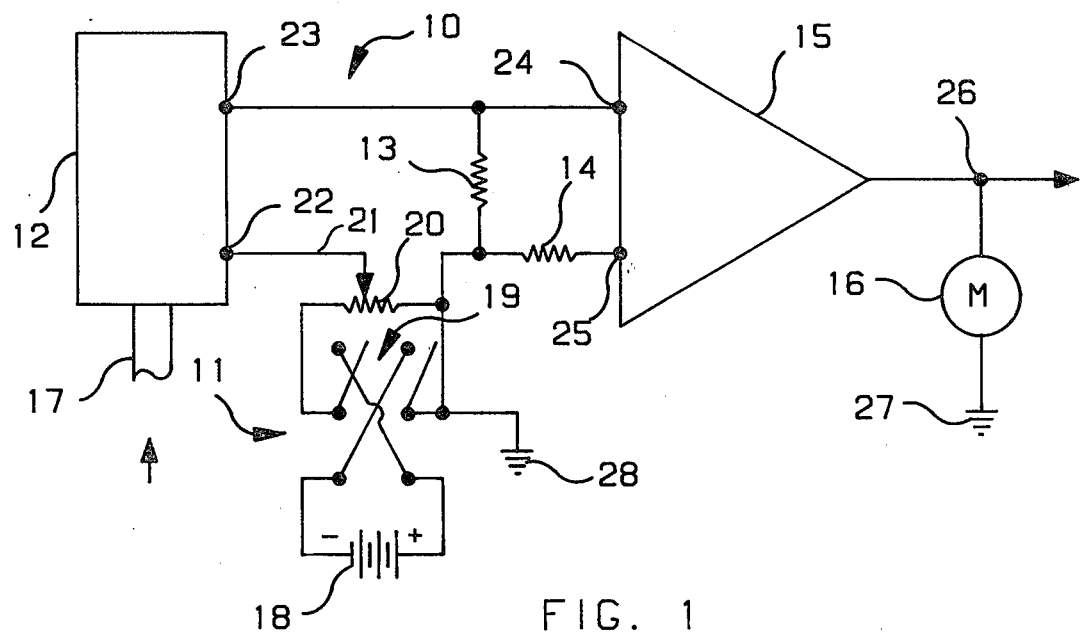
FIG. 1 is a schematic diagram of an electrical circuit depicting an ionization detector unit having an electrically powered ionization sensor cell for ionization sensing of flowing gaseous media in operative association with one form of battery powered, variable, low-voltage biasing means for stabilizing fluctuating, output voltages emitted by the ionization sensor in response to fluctuations or variations in the flow rate of gaseous media flowing through the ionization sensor cell.

Alluding initially to FIG. 1, one form of low-voltage biasing means of the present invention is shown embodied in an ionization detector unit, generally designated as 10, for monitoring the electrical ionization potential of a sampled flow, or stream, of selected gaseous media such as, for example, the surrounding ambient atmosphere to detect and signal the presence of undesirable levels, or concentrations, of alien substances and environmentally detrimental atmospheric contaminants. Briefly, the detector unit 10 includes in operative association with the low-voltage biasing means, generally designated at 11 and to be subsequently described, an ionization sensor cell 12, electrical resistance elements 13 and 14, amplification means such as a amplifier 15, and a millivoltmeter 16 for metering, after preamplification by amplifier 15, the output voltage emitted by the sensor cell 12 in response to electrical energy potential generated by ionization of the gaseous media flowing at fluctuating, or variant, rates of flow through the sensor cell 12 from a supply conduit 17 interconnecting the sensor cell to a suitable aspirating pump, not shown.

In the embodiment depicted in FIG. 1, the low-voltage biasing means 11 includes a bias battery 18 of 2.0 volt output which is connected through a reversing switch at 19 for quick conversion between positive or negative voltage polarity output. The bias of battery 18 is varied to one of the output terminals, or electrodes 22 and 23 of sensor cell 12 by means of a 1 megohm, variable resistor 20 interconnected on one side to one side of the reversing switch 19 and on the other side through connection 21 to sensor cell electrode 22. Resistance elements, or resistors 13 and 14, are provided to match the impedance of the circuit and are connected between the load side of the variable resistor 20 and the preamplifier 15 input terminals 24 and 25, respectively. With one terminal of the millivoltmeter 16 connected to the output circuit of the preamplifier, as at 26, and the other millivoltmeter terminal electrically grounded, as at 27, and with the reversing switch 19 suitably grounded, as at 28, the detector unit 10 was subjected to testing under varying flow rate and varying bias voltage conditions.

Figure 2:
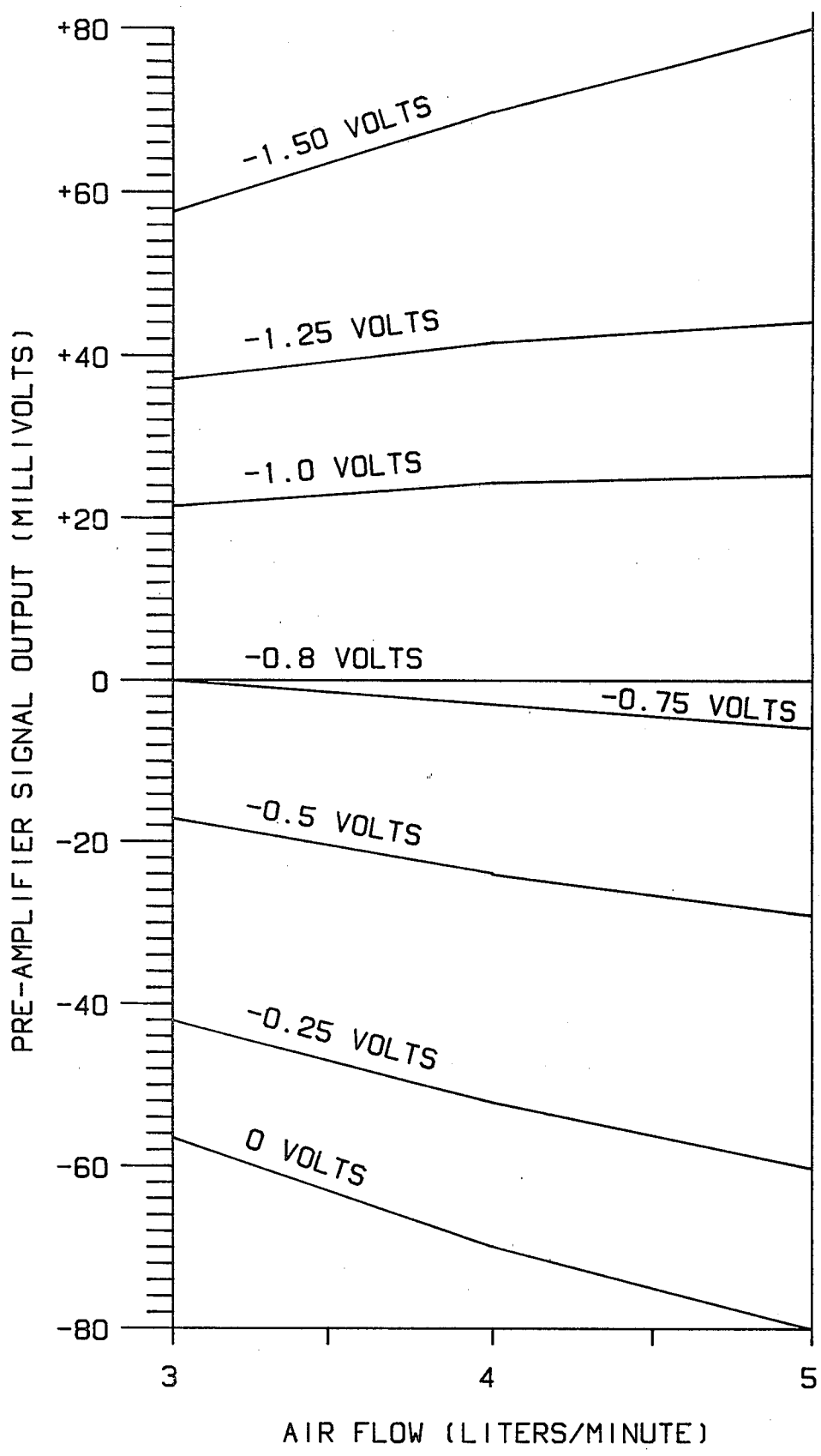
FIG. 2 is a graphic representation depicting the functional interrelationship between variations, or fluctuations, in the rate of flow of the gaseous medium, such as air, and the preamplified output signal emitted in response to such airflow variations, or fluctuations, when a series of bias voltages are impressed upon the sensor-cell, output signal.

With a variable pump that enabled the rate of flow of input air delivered to the sensor cell 12 to be adjusted from 3-5 liters per minute, operational tests were conducted which provided the data shown in FIG. 2. Different cell, bias settings were made by means of the variable resistor 20 and for each such setting, the airflow in liters per minute was varied and measurements so made for flow rates of 3, 4 and 5 liters per minute were plotted in the manner depicted in FIG. 2.

As is clearly indicated by FIG. 2, it was readily discernible that the optimum bias voltage for minimizing, or nullifying, voltage fluctuations from the sensor cell over a flow rate range of 3-5 liters per minute was −0.8 volts. As graphically indicated, the preamplified output voltage emitted from the ionization sensor cell 12, as measured by the millivoltmeter 16, remained constant at about a zero millivolt reading at respective air flows of 3, 4 and 5 liters per minute while a bias voltage of −0.8 volts was impressed upon output terminal 22 of the sensor cell. By comparison, other bias voltages applied at 0.25 volt increments over a range of from 0 to −1.50 volts were progressively ineffective (i.e., output voltages were progressively less constant) as the voltage differential between the −0.8 volt benchmark level and the other bias voltages increased. Moreover, it will be observed that the last-mentioned comparison is valid for bias voltages which were both higher and lower than the −0.8 volt level.

While the above technique has been described with respect to one specific range of variant airflow rates and to one specific ionization sensor cell, it will be readily appreciated and understood that the same technique is suitable for determining the optimum bias voltage for nullifying output voltage fluctuations resulting from variations in flow rates in most any size ionization sensor cell.

Once the best operating bias has been determined for effectively eliminating fluctuations and/or variations in the sensor cell output signal over the desired or potential range of variable rates of airflow, permanent biasing can be imposed at one electrode of the cell.

Figure 3:
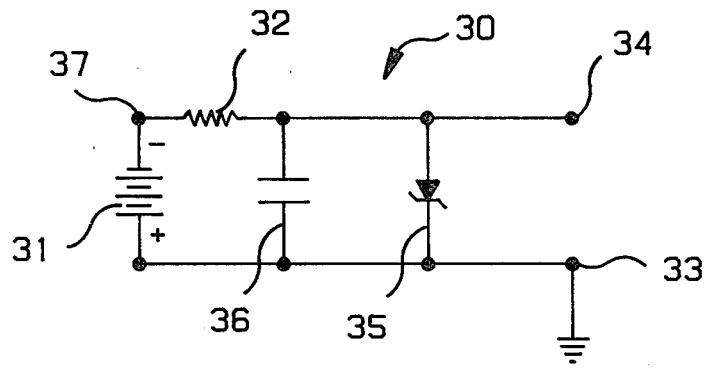
FIG. 3 is a schematic electrical circuit diagram depicting another form of battery-powered, low-voltage, biasing device for imparting a preselected, nonvariable, bias voltage upon the ionization sensor cell of FIG. 1 and having a bias voltage preselected, in accordance with the concepts and features of the present invention, to impress an optimum stabilizing bias upon the output signal of the ionization sensor cell.

One preferred form of permanent biasing unit for a sensor cell of the type described above is schematically depicted in FIG. 3. As shown, the permanent system, generally indicated as 30, comprises a bias battery 31 of 2 volts output voltage and having a positive ground terminal 33 and a negative output terminal 34 connected in series with a current limiting resistor 32 providing an electrical resistance of predetermined value to impart the desired bias voltage necessary to obviate flow-rate related voltage fluctuations emitted from the sensor cell, and which in the case of the tested, sensor cell described above would be −0.8 volts. To assure constant bias-voltage output, a zener diode 35 is preferably connected to and between the load side of the resistor 32 and the grounded terminal 33 of the bias battery 31. Optionally, a suitable capacitor 36 may additionally be connected across the terminals 33 and 34 and in parallel with the zener diode 35.

Figure 4:
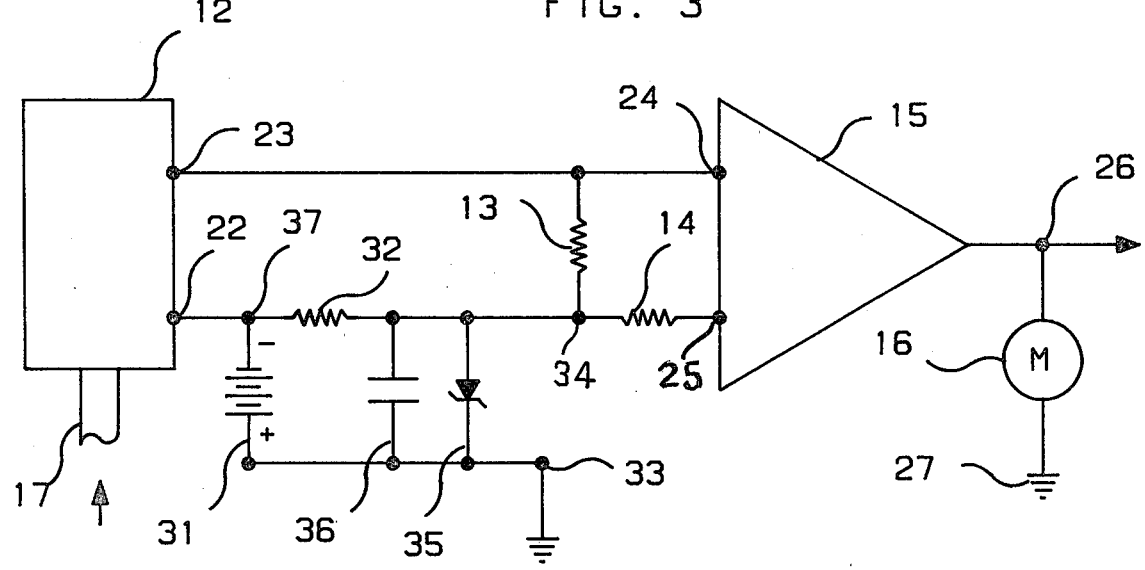
FIG. 4 is another schematic electrical diagram similar to FIG. 1, but showing the biasing device of FIG. 3 replacing the variable, low-voltage, biasing device depicted in FIG. 1.

As thus assembled, the permanent biasing unit 30 may, as shown in FIG. 4, replace the variable voltage biasing unit 11 of FIG. 1. Such replacement is expeditiously achieved by merely connecting the appropriate one of the bias battery terminals, which for the above-tested sensor cell would be the negative battery terminal 37, to one of the sensor cell electrodes, such as electrode 22, and by connecting the ungrounded output terminal to a common electrical connection leading to resistors 13 and 14.

From the foregoing, it will be readily apparent to those skilled in the art that alternative means of determining the optimum bias voltage for compensating against voltage fluctuations attributable to variations in the flow rate of gaseous media through the ionization sensor cell may be utilized provided, however, that the means or method so employed includes the provision of a capability for varying the bias applied to the output voltage of the sensor cell and the further capability of monitoring the biased output voltage emitted by the sensor cell.

Also, it will be readily apparent that an ionization sensor cell having an output voltage biased to a stabilized condition in accordance with the present invention will permit highly reliable monitoring and detection of compositional changes which may occur in the gaseous media being sampled by the cell. Moreover, such reliability is attained by use of a small, lightweight system which is particularly suitable for personal field use in providing a means of detection and warning of potentially dangerous atmospheric contaminants.

Of course, it will also be appreciated that the above features and advantages are attainable with either a variable bias system such as depicted in FIG. 1 or with a fixed bias system as depicted in FIG. 4. Moreover, it will be further appreciated that a plurality of ionization sensor cells may be utilized in combination and biased by one or more biasing systems employing the innovative concepts of the present invention. Thus, it will, of course, be understood that various details of construction, combination, assembly and methods of use may be modified throughout a wide range of equivalents, and it is, therefore, not the purpose to limit the scope of the present invention otherwise than as may be necessitated by the scope of the appended claims.

I claim:

1. For use with an ionization detector for monitoring gaseous media and detecting the presence of undesirable constituents therein, the combination comprising:

an ionization sensor cell for receiving a flow of sampled gaseous media therein and continuously sensing the ionization level thereof and for emitting electrical output voltage variations proportionate in voltage value to the levels of ionization sensed in the gaseous media, said cell being sensitive and responsive to variations in the rate of flow of the gaseous media being received therein and in consequence of such sensitivity and responsiveness thereby also emitting output voltage variations resulting from variations in the rate of flow of the gaseous media; and means for compensating for variations in the electrical output voltage emitted by said sensor cell as a result of variations in the rate of flow of the gaseous media being sensed by said cell, said compensating means including voltage biasing means for impressing a bias voltage upon the output voltage of said cell of sufficient extent to nullify output voltage variations emitted by said cell as a consequence of variations in the flow rate of the gaseous media being sensed by said cell.

2. The combination as defined in claim 1, wherein said biasing means comprises a low-voltage source providing a grounded and an ungrounded terminal, and a current limiting electrical resistance element interconnected between said ungrounded terminal and an output voltage terminal of said sensor cell.

3. The combination as defined in claim 2, wherein said electrical resistance element is a variable resistor for selectively varying the biasing voltage from said low-voltage source sufficiently to compensate for variations in the output voltage emitted by said sensor cell as a consequence of variations in the flow rate of the gaseous media being sensed by said cell.

4. The combination as defined in claim 2, wherein said biasing means further includes a zener diode interconnected between the load side of said current limiting resistance element and the grounded terminal of said low-voltage source.

5. The combination as defined in claim 4, wherein said biasing means includes a capacitor interconnected in parallel with said zener diode.

6. The combination as defined in claim 2, 3, 4 or 5, wherein said low-voltage source is a battery.

7. An ionization detector for monitoring gaseous media and detecting the presence of undesirable constituents therein, said detector comprising, in combination:

an ionization sensor cell for receiving a flow of sampled gaseous media therein and continuously sensing the ionization level thereof, said cell including an output terminal for emitting an electrical output proportionate in value to the levels of ionization sensed in the gaseous media, said cell being sensitive and responsive to variations in the rate of flow of the gaseous media being received therein and in consequence of such sensitivity and responsiveness thereby also emitting electrical output variations resulting from variations in the rate of flow of the gaseous media;

metering means having an input terminal interconnected with the output terminal of said cell for metering the electrical output emitted by said cell and thereby providing an indication of the ionization level of the gaseous media being sensed by said cell, said metering means also being responsive to variations in the electrical output emitted by said cell in response to variations in the rate of flow of the gaseous media;

means for compensating for those variations in the electrical output emitted by said sensor cell as a result of variations in the rate of flow of the gaseous media being sensed by said cell, said compensating means including voltage biasing means interconnected between the output terminal of said cell and the input terminal of said metering means for impressing a bias voltage upon the electrical output of said cell of sufficient extent to nullify the electrical output variations emitted by said cell as a consequence of variations in the flow rate of the gaseous media being sensed by said cell.

8. An ionization detector as defined in claim 7, wherein said compensating means comprises a low-voltage, battery-powered, electrical, biasing circuit for biasing the electrical output voltage emitted by said sensor cell.

9. An ionization detector as defined in claim 7, wherein said biasing circuit includes a low-voltage source providing a grounded and an ungrounded terminal and a current limiting electrical resistance element interconnected between the output terminal of said sensor cell and the ungrounded terminal of said low-voltage source.

10. An ionization detector as defined in claim 9, wherein said electrical resistance element is a variable resistor for selectively varying the biasing voltage of said biasing circuit sufficiently to compensate for variations in the electrical output emitted by said sensor cell as a consequence of variations in the flow rate of the gaseous media being sensed by said cell.

11. An ionization detector as defined in claim 9, wherein said biasing circuit includes a zener diode interconnected between the load side of said current limiting resistor and the grounded terminal of said low-voltage source.

12. An ionization detector as defined in claim 11, wherein said biasing circuit includes a capacitor interconnected in parallel with said zener diode.

13. An ionization detector as defined in claim 12, wherein said biasing circuit is adapted to compensate for variations in the rate of flow of the gaseous media being sensed by said cell throughout a flow rate variation in the range of about three to five liters per minute.

14. An ionization detector as defined in claim 13, wherein said low-voltage source provides an output voltage of about two volts and wherein said electrical resistance element provides a resistance of about one megohm.

15. An ionization detector as defined in claim 9, 10, 11, 12, 13 or 14, wherein said low-voltage source is a miniature battery.

16. A detector for use in detecting harmful constituents in gases and vapors supplied to said detector at fluctuating rates of flow, said detector comprising:

an ionization sensor cell for receiving and ionizing said gases and vapors at said fluctuating rates of flow, said sensor cell having a pair of output electrodes and being operative to produce an electrical output signal from said electrodes, said output signal varying in magnitude in proportion to the ionization level of the gases and vapors being received by said sensor cell and also varying in magnitude in proportion to the extent of the variations in the rate of flow of the gases and vapors being received by said sensor cell;

an electrical bias means interconnected to one of said electrodes for stabilizing the variations in magnitude of that portion of the output signal from said cell occurring as a result of variations in the rate of flow of said gases and vapors;

means interconnected to said output electrodes for amplifying said stabilized output signal; and monitoring means for monitoring the amplified signal.

17. A detector as defined in claim 16, wherein the electrical bias means comprises a grounded circuit having a power means connected with a zener diode through a limiting resistor.

18. A process for compensating for variations in the electrical output from an ionization sensor cell for receiving and ionizing gases and vapors supplied to the sensor cell at varying rates of flow causing said variations, said process comprising the steps of:

determining the range of the variations in the rates of flow of the gases and vapors supplied to said sensor cell;

supplying said gases and vapors to said sensor cell at a plurality of different rates of flow within the determined range of variations in the rates of flow thereof;

separately impressing a plurality of different low-voltage bias voltage upon the electrical output from said sensor cell while said gases and vapors are being supplied thereto at each of said different rates of flow;

monitoring the electrical output of said sensor cell for each of said different rates of flow and different bias voltages to determine the extent of variation in the electrical output for each variation in bias voltage and rate of flow; and continuing to impress different bias voltages upon the electrical output of said sensor cell at each of said different rates of flow until attaining a stable electrical output from said sensor cell.

19. A process as defined in claim 18, including interconnecting said sensor cell with a source of constant low-voltage bias voltage providing a bias voltage corresponding to that bias voltage at which a stable electrical output was attained.

* * * * *